(12) United States Patent
Bach

(10) Patent No.: US 6,458,555 B1
(45) Date of Patent: Oct. 1, 2002

(54) CYTOLOGIC METHOD OF EXAMINING MUCOUS MEMBRANES

(76) Inventor: Gerd Bach, Wichtelmännerweg 16, 76199 Karlsruhe (DE)

( * ) Notice: Subject to any disclaimer, the term of this patent is extended or adjusted under 35 U.S.C. 154(b) by 0 days.

(21) Appl. No.: 09/033,820

(22) Filed: Mar. 3, 1998

Related U.S. Application Data

(63) Continuation-in-part of application No. 08/697,215, filed on Aug. 21, 1996, now abandoned.

(51) Int. Cl.⁷ .............................. G01N 1/30; G01N 33/48
(52) U.S. Cl. ..................... 435/40.51; 435/40.5; 436/63; 600/562
(58) Field of Search .............................. 435/40.5, 40.51; 436/63, 64; 600/562

(56) References Cited

U.S. PATENT DOCUMENTS

| | | | |
|---|---|---|---|
| 4,759,376 A | * | 7/1988 | Stormby |
| 4,777,133 A | * | 10/1988 | Picciolo et al. |
| 5,178,859 A | * | 1/1993 | Simon et al. |
| 5,357,977 A | * | 10/1994 | Michels |

OTHER PUBLICATIONS

Maile, Laboratory Medicine: Hematology. Saint Louis, C.V. Mosby Company. 1972, pp. 1207–1208.*

Debongnie et al., 1994. Touch Cytology: a quick, simple, sensitive screening test in the diagnosis of infections of the gastrointestinal mucosa. Archives of Pathology and Laboratory Medicine 118(11): 1115–1118.*

Debongnie et al., 1992. Cytology: a simple, rapid, sensitive method in the diagnosis of *Helicobacter pylori*. Am. J. Gastroentero 87(1): 20–23.*

Faverly et al., 1990. Identification of *Campylobacter pylori* in gastric biopsy smears. Acta Cytologica 34(2): 205–210.*

DeFrancesco et al., 1993. *Helicobacter pylori* in gastroduodenal diseases: rapid identification by endoscopic brush cytology Diagnostic Cytopathology 9(4): 430–433.*

* cited by examiner

*Primary Examiner*—Christopher L. Chin
*Assistant Examiner*—James L. Grun
(74) *Attorney, Agent, or Firm*—Klaus J. Bach

(57) ABSTRACT

In a method for the cytological examination of mucous membranes, a mucous particle of about pinhead size is removed from the surface of the mucous membrane and is moved across a surface such that viscous mucous and, together therewith, the epithelial surface layer portion remain attached to the slide surface so as to form a streak preparation which is then dried for examination under a microscope. For moving the particle across the surface a needle is used which is placed with its tip onto the surface at a distance from the particle so that any pressure applied to the needle is directly transmitted to the surface but which is held at an angle of 10–30° so that the particle is contacted by the needle above its center such that a downward force is generated on the particle by which the particle is engaged with the surface in a reproducible fashion. The method can be used for the determination of fungal infections of the gastric and/or intestinal mucosa.

9 Claims, 5 Drawing Sheets

CYTOLOGIC METHOD OF EXAMINING MUCOUS MEMBRANES

This is a continuation-in-part application of U.S. application Ser. No. 08/697,215 filed Aug. 21, 1996, now abandoned.

BACKGROUND OF THE INVENTION

The present invention resides in a method of examining the mucous membranes of the gastro-intestinal system, the urinary tract and the bronchial system.

All the knowledge concerning the mucous membranes available to date has been gathered by the so-called histological method—a method of studying tissues developed by Virchow—wherein tissue is technically prepared and treated with formaldehyde. This method provides for an excellent view of the various tissue structures and facilitates a safe diagnosis on the basis of changes in the tissue structure. An important disadvantage of this method, however, is that a particular layer at the surface of the mucous membrane is lost during the technical preparation of the tissue by the histological method: By exposure to formaldehyde, the mucous coagulates and is washed away by the various solutions used during the further method steps. As a result, histological studies do not involve the particular layer at the surface of the membrane and no appropriately accurate knowledge is obtained concerning the microbiology present in this layer. Important aspects concerning this layer have therefore never come to the attention of scientists.

Another method for examining the mucous membranes resides it the so-called brush cytology. With this method, a small metal brush is introduced through an endoscope in contact with the mucous membrane surface and the membrane is streaked by the brush. However, this kind of tissue removal leads to bleeding of the injured mucous membrane so that a substantial amount of blood is mixed with a relatively small amount of tissue obtained with this method. The tissue therefore, must first be cleaned by centrifuging, whereafter only a few cells remain for studying and examination. A thorough examination or a study of the mucous-epithelial layer or of the microbiology of this layer is impossible with this method.

It is the object of the present invention to provide a method by which mucous membranes can be studied and examined while the microorganisms living on, or in, the mucous membrane are not only not destroyed, but are clearly recognizable.

SUMMARY OF THE INVENTION

In a method for the cytological examination of mucous membranes, a mucous particle of about pinhead size is removed from the surface of the mucous membrane and is moved across a slide surface. In this way, viscous mucous and, together therewith, the epithelial surface layer portion remain attached to the slide surface so as to form a streak preparation which is then dried for examination under a microscope. For moving the particle across the surface a needle is used which is placed with its tip onto the surface at a distance from the particle so that any pressure applied to the needle is directly transmitted to the slide surface. The needle is held at an angle of 10–30° so that the particle is contacted by the needle above its center such that a downward force is generated on the particle by which the particle is engaged with the surface in a reproducible fashion.

The mucous membrane is a tough viscous mucous layer which firmly adheres to the epithelial layer—in contrast to the liquid mucous within the stomach. The mucous membrane serves as protection from the aggressive stomach acids. Below this layer, microorganisms find optimal living conditions. In fact, this layer protects the microorganisms from acids and various mechanical attacks.

With the method according to the invention, a certain layer for example of the mucous membrane of the stomach can be representatively displayed and it can be shown that it contains substantial microbiological life. It can be shown with this method, that not only *Helicobacter pylori* live on the surface of the mucous membrane, but that, in the mucous epithelial layer, there are large amounts of *H. pylori,* a large growth of fungi such as yeasts of the genus Candida, and also molds. With the method according to the invention, it was finally possible to determine the cause for the chronic gastritis and of the chronic colitis.

The method according to the invention is also suitable for studying the life cycle of those microorganisms or to answer other scientific questions concerning mucous membrane problems. Although, below, the mucous membranes of the stomach are considered, the mucous membranes of the colon, of the bladder and of the bronchial tubes can also be studied with the method according to the invention even though the circumstances are different. Since in these cases, the highly viscous membrane of the stomach is not present, the microorganisms live on, and in, the epithelial cell layer of the mucous membrane.

DESCRIPTION OF THE METHOD

Figure 1:
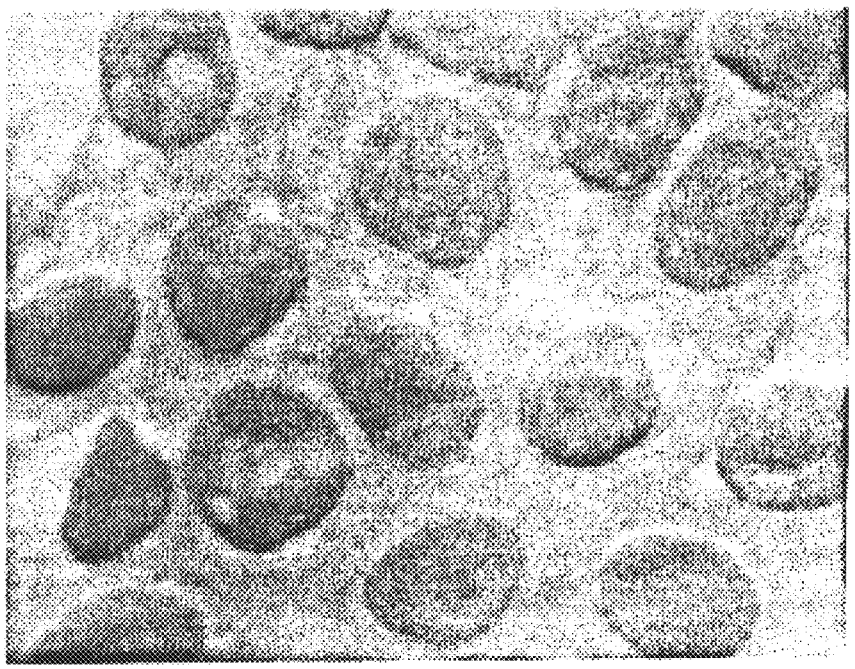
FIGS. 1 to 6 show epithelial cells and Candida fungus cells of a gastric mucous membrane.

With endoscopic examination of the stomach and intestinal tract (gastroscopy and colonoscopy) and the endoscopy of the bladder, small pin head-sized pieces of the mucous membrane are removed by pincers and are transferred directly from the pincers onto glass slides. With a thin elastic needle, the mucous membrane piece is rolled across the glass slide so as to form streaks. During this procedure, the mucous is retained on the surface of the slide leaving on the surface streaks of the width of the particle which are disposed as closely together and are as frequent as the particle is moved across the slide.

It is very important that the streaks are obtained in a way, which evenly deposits cells such that they are not damaged in the process:

A sample piece deposited on the glass slide is rolled across the glass slide using a thin elastic needle or canule having a tip which is placed onto the glass slide at a distance from the sample piece. The sample piece is about pinhead sized and the needle is held at an angle such that the sample piece is engaged by the needle above half its diameter. The needle is held at an acute angle to the glass plate of 10–30°. The pressure of the hand is transmitted by the needle to the glass slide, so that the sample piece is not squeezed in an uncontrolled manner. Only the advancing movement of the needle generates a force on the sample piece. The pinhead sized sample piece is dispose at a distance from the needle point of 0.3 to 1 cm so as to engage the sample piece at the proper level. The distance depends on the size of the sample piece. It is so selected that the needle engages the sample piece slightly above the center line in order to generate a certain force component which generates a certain engagement pressure of the sample piece with the glass slide. For generating an appropriate engagement pressure the contact point between the needle and the sample piece is above half, but not higher than three quarters of the diameter of the sample piece. In this way the sample piece is rolled over the glass slide while an epithelial cell mucous layer adheres to the glass slide with its cells undamaged.

In this depositing procedure the sample particle is partially sliding and partially rolling depending on the downward force component generated by the needle. The force component engaging the sample particle with the glass slide accordingly is variable with the height at which the sample particle is contacted by the needle. This height is dependent on the distance of the sample piece from the needle point and on the angle between the needle and the glass slide.

The engagement force component in the direction toward the glass slide depends on the consistency of the sample piece. A sample piece with a high viscosity sticky surface (mucous membrane of the stomach) requires a smaller contact force component with the glass slide; a sample piece with a low viscosity-mucous sticky surface (colon mucous membrane) requires a greater force component for engagement with the glass slide in order to achieve the desired attachment of the epithelial cell layer to the glass slide surface.

The needle point transfers the pressure of the hand directly to the glass slide surface while moving the sample piece over the glass slide. The engagement force of the sample piece with the glass slide is generated by the selection of the contact point of the needle with the sample piece in a controllable fashion independently from the feel of a person performing the procedure. In this way the cells can be deposited without damage in a reproducible fashion.

In order to obtain cells from all sides of the sample piece it is advantageous if the sample piece is moved across the glass slide in a meander-like fashion, that is the sample piece is moved forward some distance, than moved to one side, then again backward and then again to the side.

The mucous membrane epithelial cells particulary those of the stomach and intestinal mucous membranes are very soft and can easily be damaged. It is however very important to have undamaged cells available for a microscopic evaluation and distinction of the various cells (for example fungus infections or cell displasias as an early stage of cancer) as they can be obtained reliably with the method according to the present invention.

In this manner, a preparation is obtained which is air dried within a few minutes and which can then be colored. If the preparation is to be colored only at a later time, it is advantageous if the preparation is sprayed with a commercially available fixing spray, or it can be immersed for a few minutes into an alcohol solution. Without such a fixing step, essential components of the preparation, especially the *Helicobacter pylori* disappear within a few hours by the release of enzymes and can no longer be detected.

The streak preparation so generated can be colored by various methods depending on the intended use. They are suitable for the daily routine diagnosis since they can easily prepared in any laboratory. But they are also very useful for scientific precision examinations or studies. They are durable and insensitive. Disposed in Entellan under glass, their durability is without limits.

A coloration of the preparations with different colors in accordance with the May-Grünewald-Giemsa method is particularly revealing since the tissue structures can be recognized. A coloration by the Feulgen method shows the DNA and is therefore preferred if the DNA is to be studied.

The figures show preparations at various states. They were prepared by the method described above. The pictures were taken through a microscope of Zeiss by a Sony camera and transferred to a computer and printed by a color printer.

The pictures show that, with the method according to the invention, typical features of a healthy mucous membrane surface as well as typical features of an infected mucous membrane can be clearly recognized.

Especially pathogens such as Candida, can be determined in various states of development and its contribution to a particular disease can be judged in this manner.

FIG. 1 shows the epithelial cells of the gastric mucous membrane. The cell union is in dissolution, that is, the nuclei as well as the cytoplasm. The cell walls are lysed.

Figure 2:
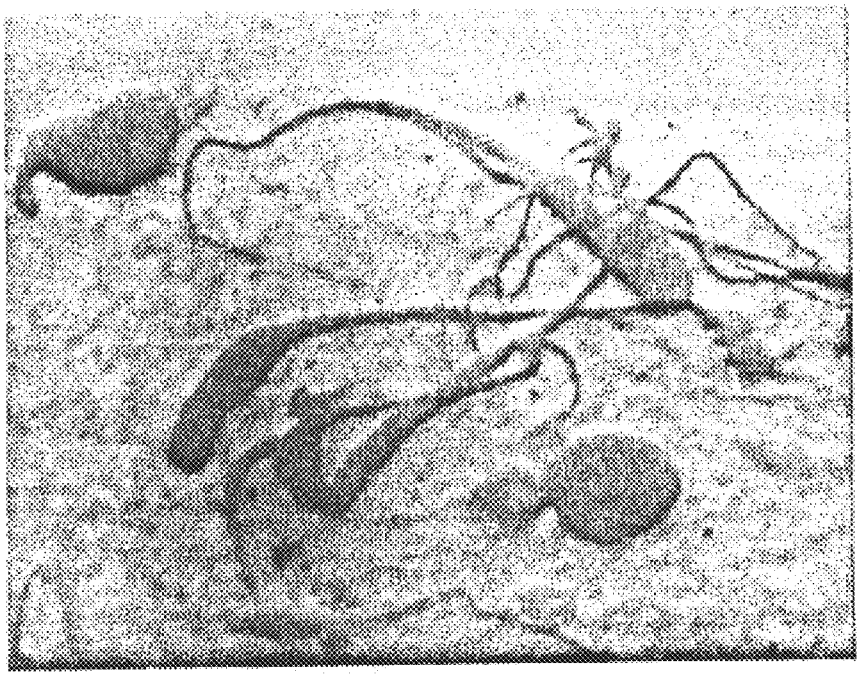

FIG. 2 shows Candida fungus cells with hyphae; one Candida cell with a hypha filament.

Figure 3:

FIG. 3 shows the development of a new fungus cell at the end of a hypha filament while the mother cell becomes smaller.

Figure 4:
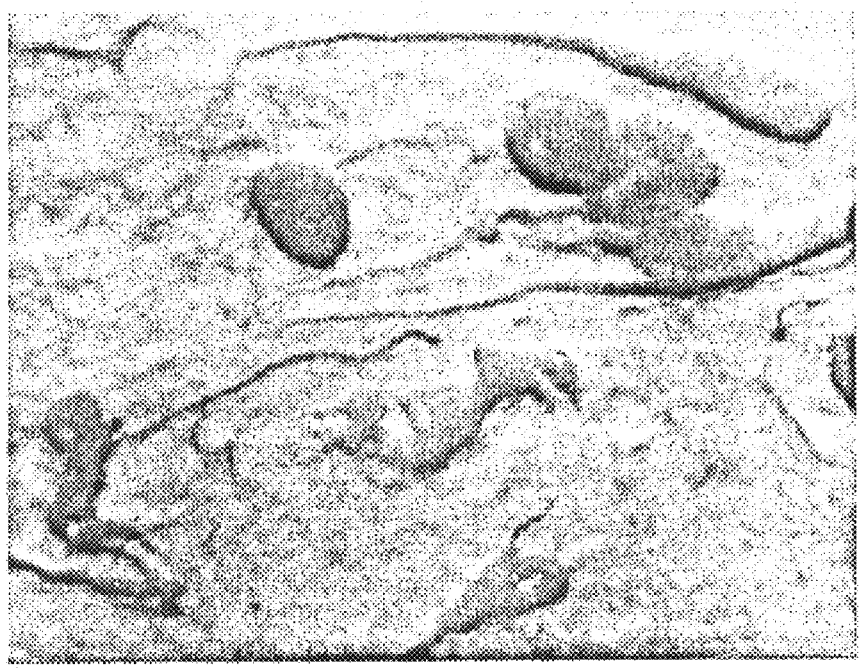
Figure 5:
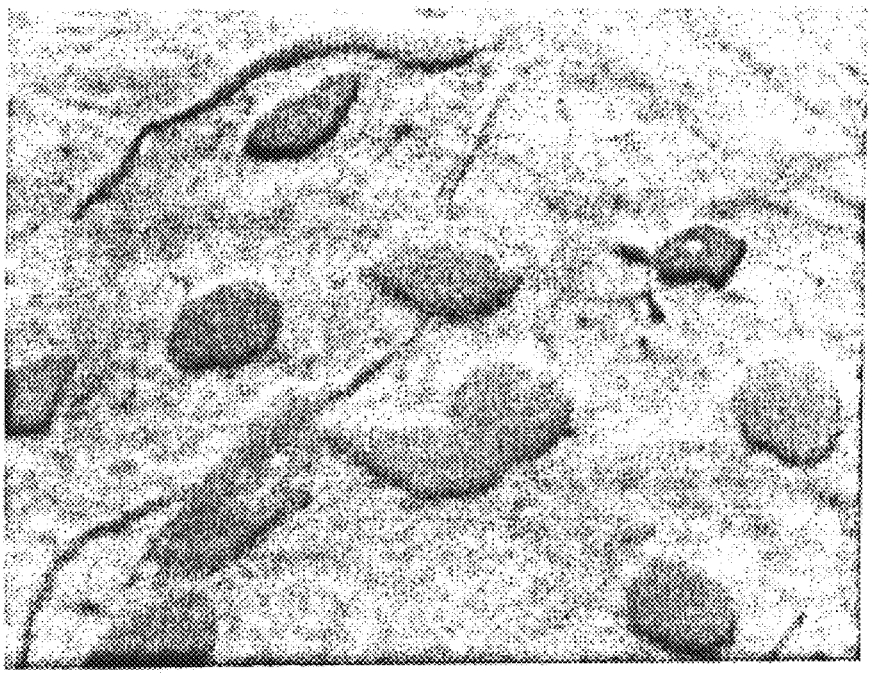

FIGS. 4 and 5 show Candida cells in active phases. In FIG. 4, the Candida cells are producing hyphae. The Candida cells in FIG. 5 are dissolving hyphae.

Figure 6:
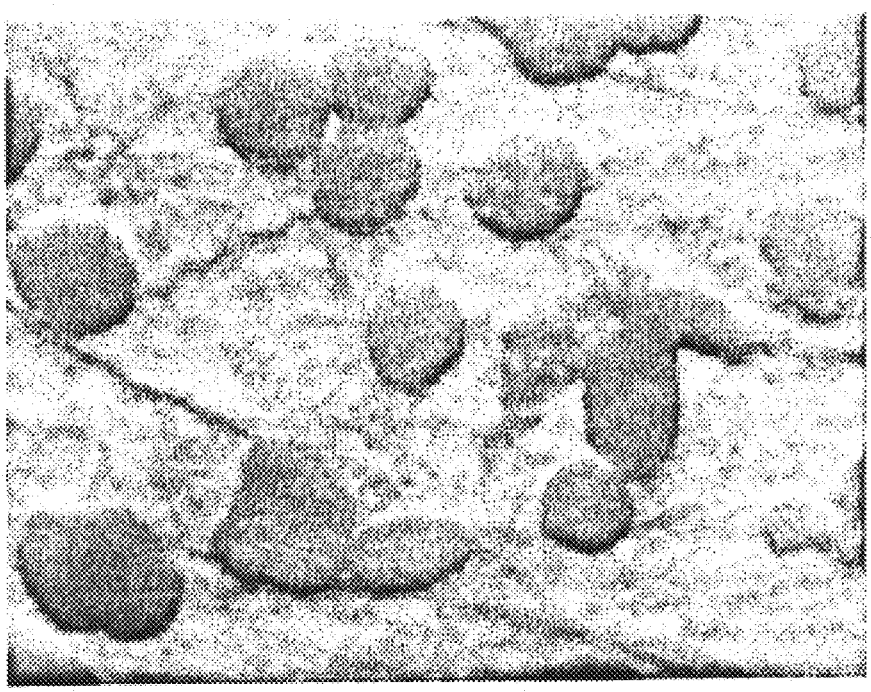

The Candida cells in FIG. 6 are in an inactive phase.

Figure 7:
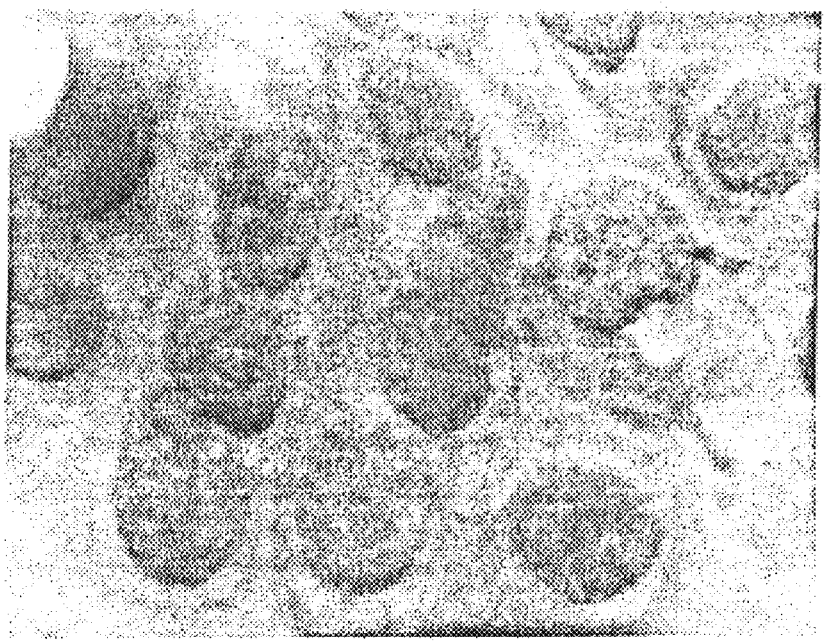
FIGS. 7 to 9 show epithelial cells and Candida fungus cells of a bronchial mucous membrane.

FIG. 7 shows the epithelial cells of the bronchial mucous membrane. The cell union is loose; the cell walls begin to dissolve; the cytoplasm is hydrated.

Figure 8:
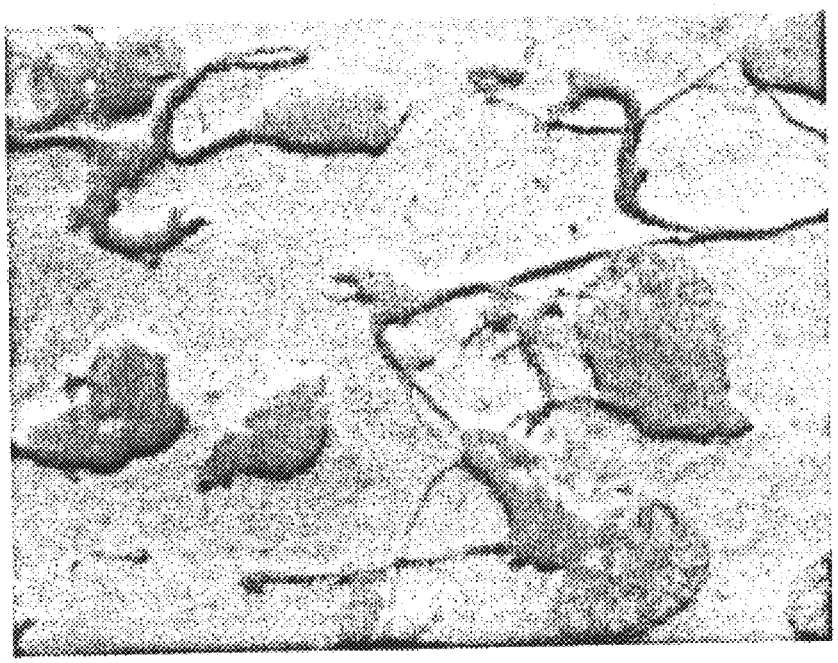

In FIG. 8, some Candida fungus cells grow short plump hyphae, others grow long thin hyphae while the nuclei of the cells of the mucous membrane are beginning to disappear. The nuclei often have no cytoplasm.

Figure 9:
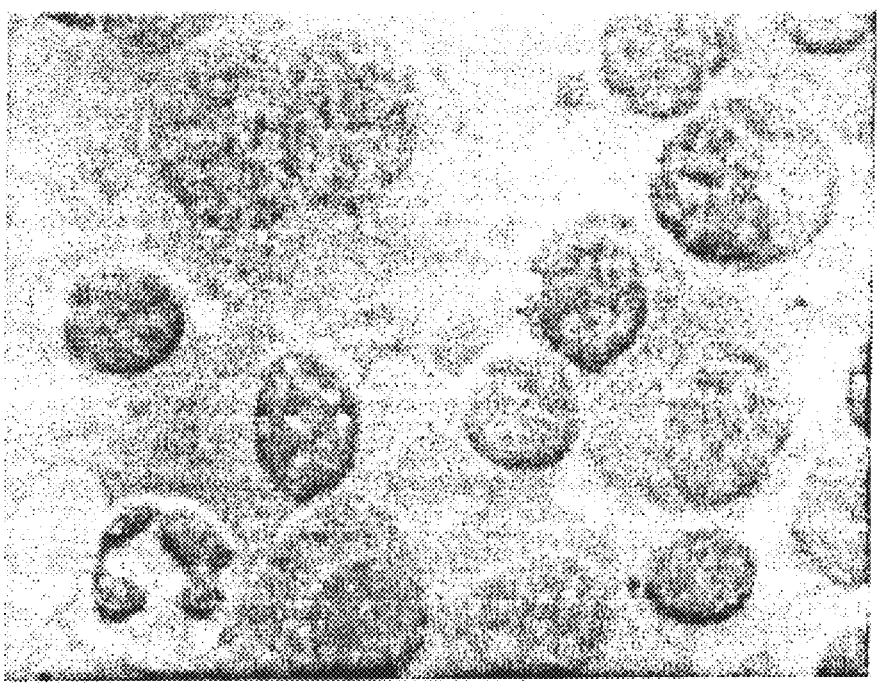

FIG. 9 shows a lymphatic reaction, which is a sign of the beginning of a defense reaction.

The pictures show a microorganism life in the gastric and bronchial mucous membranes, which has become apparent only with the method according to the present invention.

What is claimed is:

1. A method for cytological examination of a gastric or intestinal mucous membrane having an epithelial surface layer for determination of mucosal fungal infection in a patient comprising the steps of:

removing a mucous sample particle from the gastric or intestinal mucous membrane of the patient, placing the mucous particle on a surface, engaging the mucous particle by a needle having a shaft held at an angle of 10–30° with respect to said surface and a tip disposed on said surface at a surface contact point such that any downward force applied to said needle is transmitted to said surface, said needle tip being disposed on said surface at one side of, and at a distance from said mucous particle sufficient for said shaft to engage the particle at a point of contact above its center but below three fourths of its diameter such that a selectable engagement force of the particle with said surface is generated when said particle is moved by said needle across said surface, moving the mucous particle across said surface with sufficient selected engagement force such that viscous mucous and, together with the viscous mucous, an epithelial layer with undamaged cells remains attached to the surface thereby forming streak preparations, drying said streak preparations, and examining said streak preparations under a microscope to determine fungal infection of the gastric or intestinal mucosa of the patient.

2. The method according to claim 1, wherein said mucous membrane particle is repeatedly moved back and forth across said surface so as to form several streaks in side-by-side relationship.

3. The method according to claim 1, wherein said mucous membrane particle is moved across said surface in one direction, then perpendicularly to said one direction to one side and then further in said one direction and then perpendicularly to said one direction to the opposite side so that a meander-like streak pattern is formed.

4. The method according to claim 1, wherein said mucous membrane particle is moved across said slide by rolling said particle while generating an engagement pressure with said surface which depends on said point of contact of the needle shaft with said particle.

5. The method according to claim 1, including the further step of coloring said streak preparations before they are examined under the microscope.

6. The method according to claim 5, wherein said streak preparations are colored by May-Grünwald-Giemsa stain.

7. The method according to claim 1, including the further step of, after drying, spraying said streak preparations with a fixing spray.

8. The method according to claim 1, including the further step of, after drying, fixing the preparations by immersion into alcohol.

9. The method according to claim 1, including the step of after drying, encapsulating said streak preparations in a mounting medium under glass cover.

* * * * *